(12) United States Patent
Chase et al.

(10) Patent No.: US 9,885,769 B2
(45) Date of Patent: Feb. 6, 2018

(54) LOCALISED ONE-DIMENSIONAL MAGNETIC RESONANCE SPATIAL-FREQUENCY SPECTROSCOPY

(71) Applicant: Osteotronix Medical PTE Limited, Marina Bay (SG)

(72) Inventors: David R. Chase, Santa Barbara, CA (US); Timothy W. James, Santa Barbara, CA (US); Lance W. Farr, Swansea (GB)

(73) Assignee: Osteotronix Medical PTE Limited, Marina Bay (SG)

( * ) Notice: Subject to any disclaimer, the term of this patent is extended or adjusted under 35 U.S.C. 154(b) by 798 days.

(21) Appl. No.: 14/294,677

(22) Filed: Jun. 3, 2014

(65) Prior Publication Data
US 2014/0266200 A1    Sep. 18, 2014

Related U.S. Application Data

(63) Continuation of application No. PCT/US2012/068284, filed on Dec. 6, 2012.
(Continued)

(51) Int. Cl.
*G01R 33/54* (2006.01)
*G01N 24/08* (2006.01)
*G01R 33/483* (2006.01)

(52) U.S. Cl.
CPC .......... *G01R 33/54* (2013.01); *G01N 24/081* (2013.01); *G01R 33/4833* (2013.01)

(58) Field of Classification Search
USPC .................. 324/300–322; 600/407–435; 382/128–131, 155, 158
See application file for complete search history.

(56) References Cited

U.S. PATENT DOCUMENTS 4,468,621 A * 8/1984 Hinshaw ................ G01R 33/54
                                                            324/307
7,805,386 B2 * 9/2010 Greer .................... G06K 9/6248
                                                            382/158
(Continued)

FOREIGN PATENT DOCUMENTS

CN    101336380    12/2008
CN    101427147    5/2009
(Continued)

OTHER PUBLICATIONS

"Office Action dated Nov. 27, 2015; Chinese Patent Application No. 201280069143.7", (dated Nov. 27, 2015).
(Continued)

Primary Examiner — Melissa Koval
Assistant Examiner — Tiffany Fetzner
(74) Attorney, Agent, or Firm — Fogg & Powers LLC

(57) ABSTRACT

A method of assessing a spatial frequency distribution within a sample comprising subjecting the sample to magnetic resonance excitation, receiving an echo signal from the sample while the sample is subjected to a magnetic field gradient, applying an invertible linear transform to the echo signal, identifying a region of interest in the transformed echo signal and deriving a corresponding window function, applying the window function (in the signal or transform domain) to the echo signal to remove echo signal coming from regions of the sample outside of the region of interest, and analyzing the one dimensional spatial frequency content in the windowed echo signal in order to access a one dimensional spatial frequency distribution within the region of interest within the sample without creating an image.

7 Claims, 2 Drawing Sheets

Related U.S. Application Data

(60) Provisional application No. 61/567,511, filed on Dec. 6, 2011.

(56) References Cited

U.S. PATENT DOCUMENTS

| | | | | |
|---|---|---|---|---|
| 7,932,720 | B2* | 4/2011 | James | A61B 5/055 |
| | | | | 324/303 |
| 8,041,651 | B2* | 10/2011 | Greer | G06K 9/6248 |
| | | | | 382/158 |
| 2006/0155186 | A1 | 7/2006 | James | |
| 2006/0186882 | A1* | 8/2006 | Walsh | G01R 33/3415 |
| | | | | 324/309 |
| 2006/0229519 | A1 | 10/2006 | Fujiwara et al. | |
| 2007/0167717 | A1* | 7/2007 | James | A61B 5/055 |
| | | | | 600/407 |
| 2008/0152217 | A1* | 6/2008 | Greer | G06N 3/04 |
| | | | | 382/155 |
| 2009/0285462 | A1* | 11/2009 | Drabycz | G06K 9/527 |
| | | | | 382/128 |
| 2010/0013475 | A1 | 1/2010 | Kimura | |
| 2010/0316283 | A1* | 12/2010 | Greer | G06N 3/04 |
| | | | | 382/155 |
| 2011/0142316 | A1* | 6/2011 | Wang | G06T 11/006 |
| | | | | 382/131 |
| 2014/0266200 | A1* | 9/2014 | Chase | G01N 24/081 |
| | | | | 324/309 |

FOREIGN PATENT DOCUMENTS

| | | |
|---|---|---|
| CN | 101627910 | 1/2010 |
| CN | 102089670 | 6/2011 |
| JP | 2006-288504 | 10/2006 |
| JP | 2009-517134 | 4/2009 |
| WO | WO-2007/062255 | 5/2007 |
| WO | WO-2007/122553 | 11/2007 |
| WO | WO-2010/004464 | 1/2010 |
| WO | WO-2012/120358 | 9/2012 |

OTHER PUBLICATIONS

"Office Action dated Aug. 22, 2016; Chinese Patent Application No. 201280069143.7", (dated Aug. 22, 2016).

"Office Action dated Oct. 25, 2016; Japanese Patent Application No. 2014-546086", (dated Oct. 25, 2016).

"Communication Pursuant to Rules 161(1) and 162 EPC dated Nov. 21, 2014; European Patent Application No. 12813603.3", (dated Nov. 21, 2014).

Liang, Zhi-Pei, et al., "Principles of Magnetic Resonance Imaging, A Signal Processing Perspective", *IEEE Press Marketing, The Institute of Electrical and Electronics Engineers, Inc., New York*, (2000), pp. 118, 166.

Welch, Peter D., "The Use of Fast Fourier Transform for the Estimation of Power Spectra: A Method Based on Time Averaging Over Short, Modified Periodograms", *IEEE Transactions on Audio and Electroacoustics*, vol. AU-15, No. 2, (Jun. 1967), pp. 70-73.

"International Search Report and Written Opinion of the International Searching Authority dated Feb. 27, 2013, International Application No. PCT/US2012/068284", (dated Feb. 27, 2013).

Bourgeat, Pierrick, et al., "MR image segmentation of the knee bone using phase information", *Medical Image Analysis*, vol. 11, No. 4, (Mar. 30, 2007), pp. 325-335.

Cardenas-Blanco, Arturo, et al., "Noise in Magnitude Magnetic Resonance Images", *Concepts in Magnetic Resonance, Part A*, vol. 32A, No. 6, (Nov. 1, 2008), pp. 409-416.

Yang, Qing X., et al., "Two dimensional prolate spheroidal wave functions for MRI", *Journal of Magnetic Resonance*, vol. 158, No. 1-2, (Sep. 1, 2002), pp. 43-51.

* cited by examiner

LOCALISED ONE-DIMENSIONAL MAGNETIC RESONANCE SPATIAL-FREQUENCY SPECTROSCOPY

CROSS-REFERENCE TO RELATED APPLICATIONS

This application is a continuation of International Application No. PCT/US2012/068284 filed Dec. 6, 2012 which claims the benefit of U.S. Provisional Patent Application No. 61/567,511 filed Dec. 6, 2011.

BACKGROUND OF THE INVENTION

1. Field of the Invention

The present invention relates to the field of fine structures characterized by magnetic resonance and to a method for processing magnetic resonance signals.

2. Prior Art

U.S. Pat. No. 7,932,720 describes a method for measurement of biologic textures too fine to be resolved by conventional magnetic resonance imaging, providing a quantitative measure of the characteristic spatial wavelengths of these textures. In its simplest form the method consists of acquiring finely-sampled spatially-encoded magnetic resonance echoes along an axis of a selectively-excited inner-volume positioned within the biologic tissue to be analyzed. Signal analysis yields spectra of textural wavelengths within various sub-regions along the spatially encoded axis of the selected tissue volume.

Filtering techniques have been used in the prior art to selectively analyze sub-regions (regions of interest) by windowing within the selectively excited internal volume but they are non-linear as the method involves taking the magnitude of the signal to produce a signal intensity as a function of location. This prior art method (U.S. Pat. No. 7,932,720) describes a method wherein the basic steps are as follows:
1. Subject the sample to a magnetic field;
2. Subject the sample to magnetic resonance excitation;
3. Receive an echo signal from the sample while the sample is subjected to a magnetic field gradient;
4. Fourier transform the echoes and take the magnitude to convert them into a signal intensity versus position,
5. Select a region of interest by multiplying the transformed data by a windowing function;
6. Fourier transform again, converting back into the echo domain;
7. Display the result as the magnitude of the resulting derived spectrum treating it as a measure of frequency content.

While the approach in the '720 patent provides insight into underlying structure, particularly for biological samples, it is limited due to being non-linear and restricted to the use of the nonlinear magnitude function and two Fourier transforms.

Other prior art methods based on magnetic resonance for analyzing fine textures are similar to that of the '720 patent in that they also are nonlinear as a result of taking the magnitude to generate a signal intensity vs. location. They differ from the '720 patent in that they are based on the analysis of magnetic resonance image data rather than a one dimensional signal intensity. In general the steps used by these methods are as follows:
1. Receive a multiplicity of echoes (as a result of a 2D or 3D magnetic resonance acquisition sequence),
2. Fourier transform and then take the magnitude of the echoes to convert them into a signal intensity versus position (i.e., create an image or a set of images),
3. Select a region of interest by multiplying the transformed data by a windowing function (wherein the shape and the width have been carefully chosen to optimize the signal extraction without introducing truncation artifacts, and to minimize the decrease in spectral resolution),
4. Use a Fourier or other transform again to convert back into the echo domain which is a measure of frequency content,
5. Display the result as the magnitude of the resulting derived spectra.

DETAILED DESCRIPTION OF THE PREFERRED EMBODIMENTS

Figure 1:
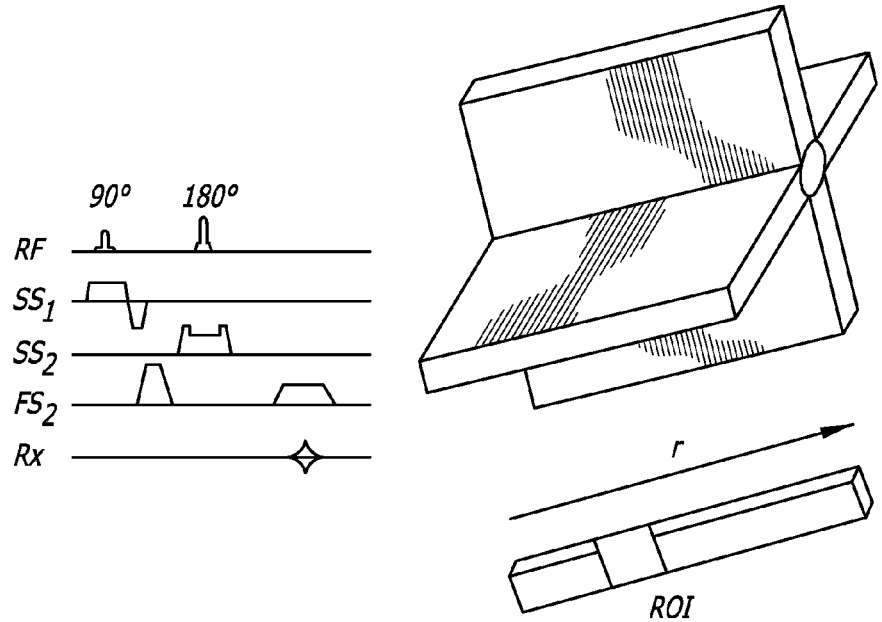
FIG. 1 is an example of a magnetic resonance technique for selectively exciting an internal volume and imposing a one dimensional spatial encode along r. A sub-region of the selectively excited internal volume is indicated by ROI (region of interest).

This invention is based on the fact that the magnetic resonance echo signal from a one dimensional frequency encoded excitation is nominally the one dimensional Fourier transform of the structure. Furthermore the one dimensional Fourier transform of the structure is the distribution (spectrum) of spatial frequencies and phases contained in the structure.

The current invention method initially proceeds like that of the '720 patent, namely by:
1. Subject the sample to a magnetic field;
2. Subject the sample to magnetic resonance excitation;
3. Receive an echo signal from the sample while the sample is subjected to a magnetic field gradient;

However, the current invention although similar to the prior art described in the '720 patent differs in a key and significant way in that the invented method uses only linear signal processes to generate spatial frequency spectra from samples of structure. Taking the magnitude of a complex signal is a non-linear operation, which loses information and introduces artifacts. To avoid these effects, the current invention utilizes a linear set of signal processing steps, which provides significant advantages including the ability to readily calculate noise statistics and an opportunity to further optimize signal to noise. Linear signal processing methods are an improvement over the prior art for a number of reasons including:
Preserving the Gaussian distribution of the noise component of the echo signal, which facilitates subsequent quantitative analysis in terms of signal-to-noise, as well as providing a basis for quantitative statistical confidence measurements.

Linearity preserves the underlying signal's complex structure, particularly in the phase space, where position is encoded. In contrast, non-linear processes, particularly magnitude operations, discard useful phase information.

Non-linear analyses can introduce artifacts in the resulting dataset which were not present in the original dataset. In contrast, linear approaches do not.

Through the use of linear transforms, the dataset can be projected into a so-called Transform Domain which can facilitate further analysis and feature identification. These, in turn, can provide direction as to how to best extract signals of interest from the original echo.

In general, the noise received as part of the MR acquisition can be well modeled as complex-valued Additive White Gaussian Noise.

As part of the MR acquisition process, an echo e[k] sequence of K samples, k=1, 2, . . . , K−1, K from MR is frequently modeled as $$e[k]=s[k]+n[k]$$

where s[k] represents the $k^{th}$ sample value of the signal, and n[k] represents the $k^{th}$ sample value of the noise received as part of the MR acquisition process. Both the signal and noise sample values are complex-values. The complex-valued nature can be made more explicit as $$e_r[k]+je_i[k]=(s_r[k]+js_i[k])+(n_r[k]+jn_i[k])$$

where the subscript 'r' indicates the "real" component", the subscript 'i' indicates the imaginary component, and 'j' is the imaginary number $\sqrt{-1}$.

The noise samples are well-modeled as having a Gaussian distribution which are independent, identically distributed, and with zero mean. More specifically, the so-called probability density function of the noise term can be expressed as $$p(n) = \frac{1}{\sigma\sqrt{2\pi}}e^{-\frac{1}{2}(n/\sigma)^2}$$

where σ represents the standard deviation, for any noise sample $n_r[k]$ or $n_i[k]$, independent of k. Further, the independence of the individual noise terms means that the value of any one of the noise samples has no influence on any of the other noise sample values.

All of this can be described more concisely in a multivariate probability density function as $$p(n) = \frac{1}{(2\pi\sigma^2)^K}e^{-(n^Tn)/2\sigma^2}$$

where n is a 2K dimensional vector (K real values, K imaginary values).

If then e[k] is subjected to a linear filtering process, the resulting noise distribution is modified, but it remains Gaussian distributed. It can be shown that the resulting multivariate probability density function can be now expressed as $$p(n) = \frac{1}{(2\pi)^K\sqrt{|\Sigma|}}e^{-\frac{1}{2}(n^T\Sigma^{-1}n)}$$

Where now Σ represents the covariance matrix, and |Σ| represents its determinant.

The value of Σ can be calculated with knowledge of the linear filter, and the variance $\sigma^2$ of the input noise process. Alternatively, Σ can be estimated, using a variety of well-established estimation algorithms. Note too that the noise distribution is independent of the signal. In other words, aside from shifting the mean of the noise to the value of the signal, the input noise variance and the linear filter determine the noise covariance; it is not affected by the signal.

The importance of being able to derive the statistics of the noise contribution is a key factor in the use of linear filtering processes, because from these, it is relatively straightforward to quantify post-processing signal-to-noise, error-bars, confidence intervals, and the like. This facilitates the use of structural spectrum analysis in a quantitative sense, which is particularly relevant for e.g. medical applications.

Finally, while it may be possible to admit certain non-linear processing steps, in addition to contending with the potential distortion of the signal itself due to the non-linearity, an additional challenge is presented in the derivation of the resulting noise distribution, and its associated dependence on the underlying signal. While there are closed-form solutions of the resulting noise distribution for some "simple" non-linear processes, they are almost always dependent upon the underlying signal in some non-trivial manner. In general, noise distributions that result from a non-linear process are frequently intractable and cannot be easily expressed in a closed-form solution.

FIG. 1 illustrates one method of performing a selective inner volume excitation and spatial encode which produces and echo from the entire inner volume. The inner volume is defined by the intersection of the two slice selective excitations and the bandwidth of the MRI scanner receiver. The Region of Interest (ROI) in this case is a segment of the inner volume which is relevant for the analysis.

Figure 2:
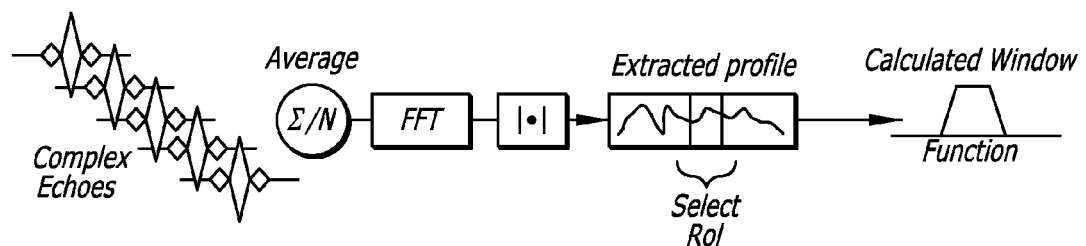
FIG. 2 shows an approach described in U.S. Pat. No. 7,932,720 to generate a window function based upon an identified Region of Interest (ROI).

FIG. 2 illustrates one method for identifying a Region of Interest (ROI) from a one dimensional plot of the signal intensity along the selectively excited internal volume (r) and then calculating a window function to filter the echo signal so that the resultant echo contains spatial frequencies exclusively from the ROI. Window functions can be generated in other ways including simply by specifying a value of "r" and window width along the selectively excited inner volume.

Figure 3:
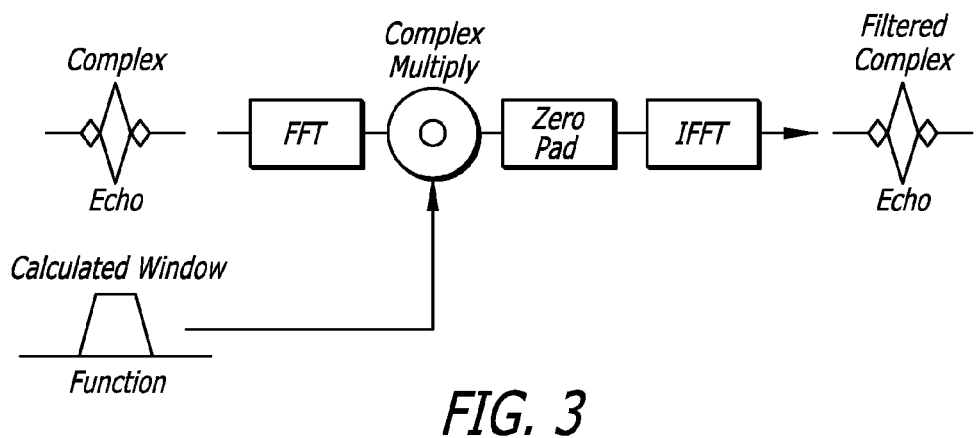
FIG. 3 shows a linear method utilizing two Fourier transformations and a complex multiplication to localize the signal to a region of interest.

FIG. 3 illustrates one method which can be used to select a specific ROI using a previously derived window function. The complex echo is converted to a generally complex-valued one dimensional profile using the Fourier Transform. The profile ROI is then selected by multiplying it by the previously derived window function. The resulting sequence is then extended in length by prepending and appending a sequence of zeroes which is used to eliminate wrap-around artifacts associated with circular convolution and to provide a "smoother" spectral representation. The resulting sequence is then converted to a generally complex-valued one-dimensional spectrum using the Inverse Fourier Transform.

Figure 4:
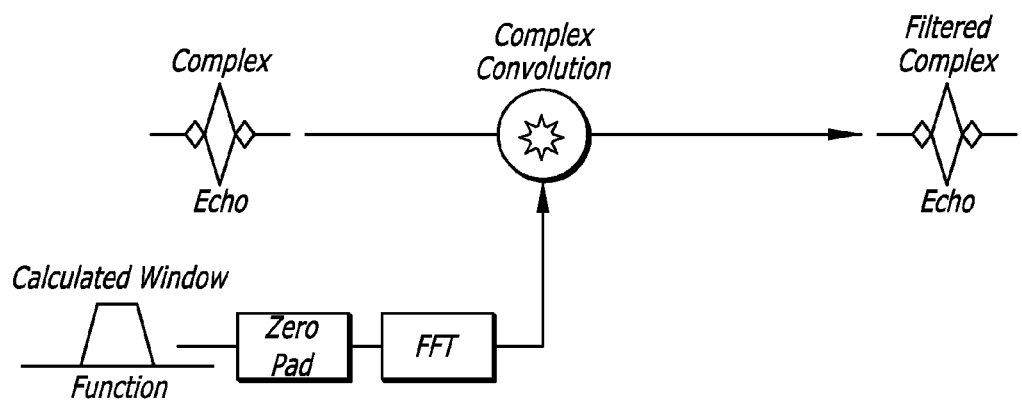
FIG. 4 shows a Linear method utilizing convolution for filtering an echo signal to localize the signal to a region of interest.

FIG. 4 illustrates another method which can also be used to select a specific ROI using a previously derived window function. In this case, the calculated window function is converted to an equivalent impulse response using zero padding followed by a Fourier Transform. The impulse response is then applied to the complex echo either directly using a complex linear convolution, or indirectly through the use of a linear filter whose impulse response is as specified.

In the above illustrations, the Fourier Transform is used as a means to convert between the echo domain and an associated Transform domain, which in this specific example nominally corresponds to the spatial distribution of the material under study. Then a "Region of Interest" is selected in that Transform domain, then the resulting spectrum is extracted.

However, both the Transform, and indeed the selection of a "Region of Interest" within that transform space, is not limited to just the selection of a subset of a region of the Fourier Transform of the echo.

In actuality, any invertible linear transformation can be used as a means to project the echo into a corresponding transform domain. An equivalent Region of Interest within that transform domain can be selected (i.e. windowed), and the residual transformed back into the echo domain, which in turn can be interpreted as the spectrum of the underlying physical representation.

Some commonly used invertible transforms include various so-called Wavelet Transforms, or z-Transforms.

The use of transforms can be useful, not only in terms of physical localization, but also for noise reduction as well.

The present invention is applicable to the assessment of any anatomical structure, whether of hard or soft tissue. Thus the present invention has a number of aspects, which aspects may be practiced alone or in various combinations or sub-combinations, as desired. While a preferred embodiment of the present invention has been disclosed and described herein for purposes of illustration and not for purposes of limitation, it will be understood by those skilled in the art that various changes in form and detail may be made therein without departing from the spirit and scope of the invention as defined by the full breadth of the following claims.

What is claimed is:

1. A method that uses a Magnetic Resonance Imaging (MRI) system in generating a spatial frequency distribution from a sample of a structure, wherein the method comprises:
   using the MRI system and its associated processors in order to perform the following:
   a) subjecting the sample to a magnetic field;
   b) subjecting the sample to magnetic resonance excitation;
   c) receiving an echo signal from the sample while the sample is subjected to a magnetic field gradient;
   d) transforming the echo signal into a corresponding transform domain, using an invertible linear transform while maintaining only linear operations in order to ensure the use of only linear signal processing steps;
   e) identifying a region of interest within resulting transform domain of d), and calculating a linear windowing function corresponding to the region of interest;
   f) applying the linear windowing function of e) to the echo signal in order to remove echo signal coming from regions of the sample outside of the region of interest;
   g) analyzing the complex-valued one dimensional spatial frequency content of the windowed echo signal obtained in f) in order to derive a one dimensional spatial frequency distribution from the region of interest within the sample of the structure without the need to create an image; and
   h) displaying a result based on the resulting derived one dimensional spatial frequency distribution.

2. The method of claim 1 wherein applying the linear windowing function comprises:
   a) taking a transform of the echo signal;
   b) complex multiplying the calculated window function by the echo signal;
   c) taking an inverse transform of the result of b).

3. The method of claim 2 wherein the transform and the inverse transform are Fourier transforms.

4. The method of claim 2 wherein the transform and the inverse transform are wavelet transforms.

5. The method of claim 2 wherein the transform and the inverse transform are z-transforms.

6. The method of claim 1 wherein the sample is subjected to a first and second magnetic resonance excitation in order to selectively excite an inner volume.

7. A method that uses a Magnetic Resonance Imaging (MRI) system in generating a spatial frequency distribution from a sample of a structure, wherein the method comprises:
   using the MRI system and its associated processors in order to perform the following:
   a) subjecting the sample to a magnetic field;
   b) subjecting the sample to magnetic resonance excitation;
   c) receiving an echo signal from the sample while the sample is subjected to a magnetic field gradient;
   d) transforming the echo signal into a corresponding transform domain using an invertible linear transform while maintaining only linear operations in order to ensure the use of only linear signal processing steps;
   e) identifying a region of interest within resulting transform domain of d), and calculating a linear windowing function corresponding to the region of interest;
   f) applying the linear windowing function of e) to the echo signal in order to remove echo signal coming from regions of the sample outside of the region of interest;
   g) analyzing the complex-valued one dimensional spatial frequency content of the windowed echo signal obtained in f) in order to derive a one dimensional spatial frequency distribution from the region of interest within the sample of the structure without the need to create an image;
   h) displaying a result based on the resulting derived one dimensional spatial frequency distribution; and
   wherein applying the linear windowing function comprises:
   i) taking the Fourier transform of the calculated window function; and
   j) taking a complex convolution of the echo signal with the transformed window function.

* * * * *